US006403597B1

(12) United States Patent
Wilson et al.

(10) Patent No.: US 6,403,597 B1
(45) Date of Patent: *Jun. 11, 2002

(54) ADMINISTRATION OF PHOSPHODIESTERASE INHIBITORS FOR THE TREATMENT OF PREMATURE EJACULATION

(75) Inventors: Leland F. Wilson, Menlo Park; Paul C. Doherty, Jr., Cupertino, both of CA (US); Virgil A. Place, Kawaihae, HI (US); William L. Smith, Montclair, NJ (US); Ibrahim AbouBakr Abdel-Hamid Abdou Ali, Mansoura (EG)

(73) Assignee: Vivus, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/888,250

(22) Filed: Jun. 21, 2001

Related U.S. Application Data (63) Continuation-in-part of application No. 09/467,094, filed on Dec. 10, 1999, which is a continuation-in-part of application No. 09/181,070, filed on Oct. 27, 1998, now Pat. No. 6,037,346, which is a continuation-in-part of application No. 08/958,816, filed on Oct. 28, 1997, now abandoned.

(51) Int. Cl.$^7$ .............................................. A61K 31/50
(52) U.S. Cl. ..................................................... 514/256
(58) Field of Search ........................................ 514/258

(56) References Cited

U.S. PATENT DOCUMENTS

| | | | |
|---|---|---|---|
| 4,507,323 A | | 3/1985 | Stern |
| 4,666,908 A | | 5/1987 | Hamilton |
| 4,940,731 A | | 7/1990 | Bick |
| 5,151,448 A | | 9/1992 | Crenshaw et al. |
| 5,250,534 A | | 10/1993 | Bell et al. |
| 5,272,147 A | | 12/1993 | Bell et al. |
| 5,276,042 A | | 1/1994 | Crenshaw et al. |
| 5,346,901 A | | 9/1994 | Bell et al. |
| 5,426,107 A | | 6/1995 | Bell et al. |
| 5,707,999 A | | 1/1998 | Cavallini |
| 5,874,437 A | | 2/1999 | Garvey et al. |
| 5,922,341 A | | 7/1999 | Smith et al. |
| 6,037,346 A | * | 3/2000 | Doherty et al. ............. 514/258 |
| 6,037,360 A | | 3/2000 | Smith et al. |
| 6,127,363 A | * | 10/2000 | Doherty et al. ............. 514/258 |
| 6,156,753 A | * | 12/2000 | Doherty et al. ............. 514/252 |
| 6,200,591 B1 | | 3/2001 | Hussain et al. |
| 6,228,864 B1 | | 5/2001 | Smith et al. |
| 8,288,064 | | 9/2001 | Watanabe et al. |

FOREIGN PATENT DOCUMENTS

| | | |
|---|---|---|
| DE | 4338948 | 5/1995 |
| DE | 19603321 | 8/1997 |
| EP | 0911333 | 4/1999 |
| EP | 0934933 | 8/1999 |
| EP | 0951908 | 10/1999 |
| WO | WO 94/28902 | 12/1994 |
| WO | WO 96/16644 | 6/1996 |
| WO | WO 96/32003 | 10/1996 |
| WO | WO 98/47557 | 10/1998 |
| WO | WO 99/21558 | 5/1999 |
| WO | WO 99/21562 | 5/1999 |
| WO | WO 99/22731 | 5/1999 |
| WO | WO 99/47505 | 9/1999 |
| WO | WO 99/56666 | 11/1999 |
| WO | WO 99/66933 | 12/1999 |
| WO | WO 00/07597 | 2/2000 |
| WO | WO 00/11002 | 3/2000 |
| WO | WO 00/14088 | 3/2000 |
| WO | WO 00/42992 | 7/2000 |
| WO | WO 00/43392 | 7/2000 |
| WO | WO 00/53148 | 9/2000 |
| WO | WO 00/56719 | 9/2000 |
| WO | WO 00/63170 | 10/2000 |
| WO | WO 00/67729 | 11/2000 |
| WO | WO 01/17521 | 3/2001 |

OTHER PUBLICATIONS

Bivalacqua et al. (1999), "Potentiation of Erectile Response and cAMP Accumulation by Combination of Prostaglandin $E_1$ and Rolipram, a Selective Inhibitor of the Type 4 Phosphodiesterase (PDE 4)," *The Journal of Urology* 162:1–8.

Boolell et al. (1996), "Sildenafil: An Orally Active type 5 Cyclic GMP–Specific Phosphodiesterase Inhibitor for the Treatment of Penil Erectile Dysfunction," *International Journal of Impotence Research* 8:47–52.

Bush et al. (1992), "Nitric Oxide is a Potent Relaxant of Human and Rabbit Corpus Cavernosum," *The Journal of Urology* 147:1650–1655.

Doherty (1997), "Oral,Transdermal, and Transurethral Therapies for Erectile Dysfunction," *Male Infertility and Dysfunction*, Springer–Verlag New York, Inc., pp. 452–467.

Martinez–Piñeiro et al. (1993), "Cyclic Guanosine Monophosphate Mediates Penile Erection in the Rat," *European Urology* 24:492–499.

Polson et al. (1996), "Cyclic Nucleotide Phosphodiesterases and Vascular Smooth Muscle," *Annu. Rev. Pharmacol. Toxicol.* 36:403–427.

Rajfer et al (1992), "Nitric Oxide as a Mediator of Relaxation of the Corpus Cavernosum in Response to Nonadrenergic, Noncholinergic Neurotransmission, " *The New England Journal of Medicine* 326(2):90–94.

Sparwasser et al. (1994), "Smooth Muscle Tone Regulation in Rabbit Cavernosal and Spongiosal Tissue by Cyclic AMP–and Cyclic GMP–Dependent Mechanisms," *The Journal of Urology* 152:2159–2163.

(List continued on next page.)

Primary Examiner—James H. Reamer
(74) *Attorney, Agent, or Firm*—Dianne E. Reed; Reed & Associates (57) ABSTRACT

A method is provided for treatment of premature ejaculation by administration of a phosphodiesterase inhibitor, e.g., an inhibitor of a Type III, Type IV, or Type V phosphodiesterase. In a preferred embodiment, administration is on as "as needed" basis, i.e., the drug is administered immediately or several hours prior to sexual activity. Pharmaceutical formulations and packaged kits are also provided.

94 Claims, 1 Drawing Sheet

OTHER PUBLICATIONS

Stief et al. (1995), "Cycli Nucleotide Phosphodiesterase (PDE) Isoenzymes in Human Cavernous Smooth Muscle: Characterization and Functional Effects of PDE–Inhibitors In Vitro and In Vivo," *International Journal of Impotence Research, Basic and Clinical Studies* 7(1):6–7.

Taher et al. (1992), "Cyclic Nucleotide Phosphodiesterase Activity in Human Cavernous Smooth Muscle and the Effect of Various Selective Inhibitors," *Internatinal Journal of Impotence Research, Basic and Clinical Studies* 4(2):11.

Taher et al. (1992), "Cyclic Nucleotide Phosphodiesterase in Human Cavernous Smooth Muscle," *World Journal of Urology* 15:32–35.

Trigo–Rocha et al. (1993), "The Role of Cyclic Adenosine Monophosphate, Cyclic Guanosine Monophosphate, Endothelium and Nonadrenergic, Noncholinergic Neurotransmission in Canine Penile Erection, " *The Journal of Urology* 149:872–877.

Truss et al. (1998), "Phosphodiesterase Inhibitors in the Treatment of Erectile Dysfunction," *Drugs of Today* 34(9), summary only.

Abdel–Hamid et al. (Feb. 2001), "Assessment of as Needed Use of Pharmacotherapy and the Pause–Squeeze Technique in Premature Ejaculation," *International Journal of Impotence Research* 13(1):41–45.

Goodman (1977), "The Management of Premature Ejaculation," *J. Int. Med. Res.* 5(Supplement 1):78–79.

Kim et al. (1998), "Treatment of Premature Ejaculation," *The Journal of Family Practice* 46(4):280–281.

Rowland et al. (1998), "The Treatment of Premature Ejaculation: Psychological and Biological Strategies," *Drugs of Today* 34(10):879–899.

St. Lawrence et al. (1992), "Evaluation and Treatment of Premature Ejaculation: A Critical Review," *Int'l J. Psychiatry in Medicine* 22(1):77–97.

* cited by examiner

FIG. 1

ADMINISTRATION OF PHOSPHODIESTERASE INHIBITORS FOR THE TREATMENT OF PREMATURE EJACULATION

CROSS-REFERENCE TO RELATED APPLICATIONS

This is a continuation-in-part of U.S. patent application Ser. No. 09/467,094, filed Dec. 10, 1999, which is a continuation-in-part of U.S. Ser. No. 09/181,070, filed Oct. 27, 1998 and issued on Mar. 14, 2000 as U.S. Pat. No. 6,037,346, which was a continuation-in-part of U.S. Ser. No. 08/958,816, filed Oct. 28, 1997, abandoned. The disclosures of each of the aforementioned applications are incorporated by reference in their entireties.

TECHNICAL FIELD

This invention relates generally to methods and pharmaceutical compositions for the treatment of premature ejaculation. More particularly, the invention relates to the use of phosphodiesterase inhibitors in such methods and compositions.

BACKGROUND

Premature ejaculation is a debilitating yet common sexual dysfunction, and has been estimated to affect at least 30 to 40 percent of men at some point in their lives (Derogatis (1980) *Med. Aspects Hum. Sexuality* 14:1168–76; Frank et al. (1978) *New Engl. J Med.* 299:111–115; Schein et al. (1988) *Fam. Pract. Res. J.* 7(3):122–134). The condition can lead to an inability to enter into or sustain relationships, can cause psychological damage to sufferers, and can also impair reproductive success.

The Diagnostics and Statistical Manual of Mental Disorders (DSM-IV) (Washington, D.C.: American Psychiatric Association, 1994) delineates three criteria for a diagnosis of premature ejaculation: (1) "persistent or recurrent ejaculation with minimal sexual stimulation before, on or shortly after penetration and before the person wishes it," which is (2) associated with "marked distress or interpersonal difficulty," and (3) not due exclusively to the "direct" effects of a "substance" (with withdrawal from opioids cited as an example). The disorder is usually primary, but can also be secondary. "Primary" premature ejaculation refers to a lifelong, typically congenital condition, while "secondary" premature ejaculation refers to a late onset condition, acquired after a period of normal functioning. Sexual dysfunctions such as premature ejaculation may also be further characterized as being generalized or limited to certain situations, and with respect to degree or frequency of the disturbance.

Premature ejaculation has historically been treated by psychosexual counseling in combination with "behavioral" therapies such as the so-called "pause" and "pause-squeeze" techniques. See St. Lawrence et al. (1992), "Evaluation and Treatment of Premature Ejaculation: A Critical Review," *Int. J. Psychiatry in Medicine* 22(1):77–97; Semans, "Premature Ejaculation: A New Approach," *Southern Medical Journal* 49:353–357, regarding the "pause" technique; and Masters and Johnson, *Human Sexual Inadequacy,* Little, Brown & Company, Boston, Mass., 1970, regarding the "pause-squeeze" technique. Any improvement resulting from the aforementioned techniques is short-lived, however, and the cooperation of a man's sexual partner is required. Typically, psychosexual counseling also requires the cooperation of the partner. Furthermore, many men may demand a quicker solution to the problem or are unwilling to attend counseling sessions. In addition, psychosexual counseling requires specialized therapists who may not be available to all patients, particularly in remote locations. Finally, counseling benefits only a subset of patients, i.e., those for whom the condition is psychogenic. Psychological therapies cannot alleviate premature ejaculation resulting from non-psychological causes.

Topical anesthetic agents and intracavernosal injection of medicaments have also been employed to treat patients suffering from premature ejaculation. However, anesthetic agents are problematic insofar as they necessarily decrease tissue sensitivity and thereby diminish sexual pleasure. Also, topical anesthetics can be transferred to sexual partners and thereby decrease their sensitivity and pleasure as well. Intracavemosal injection is associated with pain and discomfort, and is not a preferred mode of drug administration. Various devices have also been proposed to delay ejaculation; however, such devices can be awkward, inconvenient and embarrassing to use.

Methods for treating premature ejaculation by systemic administration of several different antidepressant compounds have been described (U.S. Pat. Nos. 4,507,323, 4,940,731, 5,151,448, and 5,276,042; PCT Publication No. WO95/13072). However, these drugs may not be effective for all patients, and the side effects of these drugs can halt treatment or impair patient compliance. Disease states or adverse interactions with other drugs may contraindicate the use of these compounds or require lower dosages that may not be effective to delay the onset of ejaculation.

For example, administration of the antidepressant fluoxetine has been claimed to treat premature ejaculation; see U.S. Pat. No. 5,151,448. However, the administration of fluoxetine has many undesired aspects. Patients with hepatic or renal impairments may not be able to use fluoxetine due to its metabolism in the liver and excretion via the kidney. Systemic events during fluoxetine treatment involving the lungs, kidneys or liver have occurred, and death has occurred from overdoses. In addition, numerous side effects are associated with oral fluoxetine administration include hair loss, nausea, vomiting, dyspepsia, diarrhea, anorexia, anxiety, nervousness, insomnia, drowsiness, fatigue, headache, tremor, dizziness, convulsions, sweating, pruritis, and skin rashes. Fluoxetine interacts with a range of drugs, often by impairing their metabolism by the liver.

U.S. Pat. No. 4,940,731 describes the oral or parenteral administration of sertraline for treating premature ejaculation. It has been recognized that sertraline shares many of the same problems as fluoxetine; see Martindale, The Extra Pharmacopoeia, 31st edition, at p. 333 (London: The Royal Pharmaceutical Society, 1996). Sertraline is metabolized in the liver, and is excreted in the urine and feces. Thus, patients with cirrhosis must take lower doses, and caution must be exercised when administering sertraline to patients with renal impairment. Individuals taking monoamine oxidase inhibitors cannot take sertraline due to the risk of toxicity. Side effects resulting from oral sertraline administration include nausea, diarrhea, dyspepsia, insomnia, somnolence, sweating, dry mouth, tremor and mania. Rare instances of coma, convulsions, fecal incontinence and gynecomastia have occurred in patients undergoing sertraline therapy.

U.S. Pat. No. 5,276,042 describes the administration of paroxetine for the treatment of premature ejaculation. Paroxetine is predominantly excreted in the urine, and decreased doses are recommended in patients with hepatic and renal impairments. Like sertraline, paroxetine cannot be given to patients undergoing treatment with a monoamine oxidase inhibitor. Side effects from oral administration of paroxetine include hyponatremia, asthenia, sweating, nausea, decreased appetite, oropharynx disorder, somnolence, dizziness, insomnia, tremor, anxiety, impaired micturition, weakness and paresthesia All of the known methods to treat premature ejaculation are thus problematic in one or more respects. An ideal method would not require ongoing ("chronic") drug therapy or use of active agents with numerous and/or serious side effects. An ideal method would be useful in the treatment of individuals with secondary, acquired premature ejaculation as well as those suffering from a primary, lifelong condition. The method would not involve application of anesthetic agents, intracavemosal drug administration, or use of devices, and would not require ongoing counseling sessions.

It has now been discovered by the present inventors that phosphodiesterase (PDE) inhibitors, as a class, are unexpectedly useful in treating premature ejaculation, and meet all of the aforementioned requirements. The discovery is indeed surprising insofar as PDE inhibitors—of which sildenafil citrate, commercially available as Viagra®, is a representative compound—are used to treat impotence and thus enhance sexual function, i.e., as opposed to modulating sexual function in a manner that allows delay of ejaculation.

Phosphodiesterases are a class of intracellular enzymes involved in the metabolism of the second messenger nucleotides, cyclic adenosine monophosphate (cAMP), and cyclic guanosine monophosphate (cGMP) (see, e.g., Doherty, "Oral, Transdermal and Transurethral Therapies for Erectile Dysfunction" in Male Infertility and Dysfunction, Hellstrom, ed., Chapter 34 (New York, N.Y.: Springer-Verlag, 1997)). Numerous phosphodiesterase inhibitors have previously been described in the literature for a variety of therapeutic uses, including treatment of obstructive lung disease, allergies, hypertension, angina, congestive heart failure and depression (see, e.g., Goodman and Gilman's The Pharmacological Basis of Therapeutic Ninth Edition, Chapter 34). Oral and parenteral administration of phosphodiesterase inhibitors, as alluded to above, has also been suggested for the treatment of erectile dysfunction (Doherty, supra; see also PCT Publication Nos. WO 96/16644 and WO 94/28902).

As explained by Komas et al. in *Phosphodiesterase Inhibitors*, Schudt et al., Eds., Ch. 6 (San Diego, Calif.: Academic Press, 1996), those initially working in the field partially purified what was believed to be a single enzyme responsible for specifically hydrolyzing the 3'-bond of cyclic nucleotides. However, it later became clear that multiple forms of phosphodiesterase inhibitors were present in different tissues; the enzymes were classified into three major groups, one of which exhibited high affinity for cAMP and designated as the "low $K_m$" cAMP PDE. This "low $K_m$" cAMP PDE was ultimately discovered to consist of two distinct isoenzymes having entirely different properties, including physical properties, kinetic characteristics and inhibitor specificities. One isoenzyme was found to be very sensitive to inhibition by cilostamide and cGMP, and is now known as the cAMP-specific, cGMP-inhibited cyclic nucleotide phosphodiesterase (cGI-PDE) or PDE III, while the second isoenzyme was classified as PDE IV. Komas et al., supra.

The phosphodiesterases have now been classified into ten major families, Types I–XI, based on amino acid or DNA sequences. The members of the family vary in their tissue, cellular and subcellular distribution, as well as their links to cAMP and cGMP pathways. For example, the corpora cavernosa contains: Type III phosphodiesterases, which as explained above are cAMP-specific cGMP inhibitable; Type IV phosphodiesterases, the high affinity, high-specificity cAMP-specific form; and Type V phosphodiesterases, one of the cGMP-specific forms.

Accordingly, the present invention is addressed to the limitations of the prior art, and provides a novel treatment for individuals suffering from either primary or secondary premature ejaculation, wherein drug administration may be on an "as-needed" basis rather than necessarily involving chronic pharmacotherapy, and does not involve use of anesthetic agents, intracavemosal drug administration, or use of devices. To the best of applicants' knowledge, the present method of treating premature ejaculation is novel and completely unsuggested by the prior art.

SUMMARY OF THE INVENTION

It is a primary object of the invention to address the above-described need in the art by providing a novel method for the treatment of premature ejaculation by administering an effective amount of a phosphodiesterase inhibitor to an individual in need of such therapy, wherein the term "phosphodiesterase inhibitor" includes phosphodiesterase inhibitors per se as well as pharmaceutically acceptable (and pharmacologically active) salts, esters, amides, prodrugs, active metabolites and other derivatives thereof.

It is another object of the invention to provide such a method wherein the phosphodiesterase inhibitor is administered orally.

It is another object of the invention to provide such a method wherein the phosphodiesterase inhibitor is administered transmucosally, e.g., via the sublingual, buccal, nasal, transurethral or rectal routes, or via inhalation.

It is another object of the invention to provide such a method wherein the phosphodiesterase inhibitor is administered topically, transdermally, parenterally, or by other routes.

It is still another object of the invention to provide such a method wherein the phosphodiesterase inhibitor is a Type III inhibitor, a Type IV inhibitor, a Type V inhibitor, or a nonspecific phosphodiesterase inhibitor.

It is yet another object of the invention to provide such a method wherein the phosphodiesterase inhibitor is a Type V inhibitor.

It is a further object of the invention to provide such a method wherein drug administration is on an as-needed basis.

It is still a further object of the invention to provide such a method wherein the active agent is administered in a controlled release formulation.

It is yet a further object of the invention to provide such a method wherein the controlled release formulation is a sustained release formulation and/or a delayed release formulation.

It is an additional object of the invention to provide such a method wherein the controlled release formulation is a sustained release formulation that provides drug release over a time period in the range of about 4 to about 48 hours.

It is still an additional object of the invention to provide a composition containing an amount of a phosphodiesterase inhibitor effective for the treatment of premature ejaculation.

It is another object of the invention to provide a packaged kit comprised of a container housing a phosphodiesterase inhibitor formulation as provided herein and instructions for administering the formulation in a manner effective to treat premature ejaculation.

Additional objects, advantages and novel features of the invention will be set forth in part in the description which follows, and in part will become apparent to those skilled in the art upon examination of the following, or may be learned by practice of the invention.

In a first aspect of the invention, a method is provided for the treatment of an individual prone to or suffering from premature ejaculation, the method comprising administering to an individual in need of such treatment a pharmaceutical formulation containing a therapeutically effective amount of an active agent selected from the group consisting of phosphodiesterase inhibitors and pharmaceutically acceptable, pharmacologically active salts, esters, amides, prodrugs, active metabolites, and other derivatives thereof. Administration of the pharmaceutical formulation may be on an "as-needed" basis or within the context of an ongoing dosage regimen. By "as-needed" dosing, also known as pro re nata dosing, is meant the administration of a single dose of the active agent at some time prior to anticipated sexual activity. Administration can be immediately prior to sexual activity, or up to about 2 or 3 hours prior to anticipated sexual activity, although with sustained release dosage forms, a single dose can provide therapeutic efficacy over an extended time period in the range of about 4 to 48 hours, depending on the formulation. Drug delivery may be accomplished through any mode of administration, including, but not limited to, the oral and transmucosal routes.

In a further aspect of the invention, pharmaceutical formulations are provided for carrying out the method of the invention. The pharmaceutical formulations comprise a therapeutically effective amount of an active agent as provided herein, a pharmacologically acceptable carrier or vehicle, generally a carrier or vehicle suitable for transmucosal drug administration, and, optionally, an enhancer. Other types of components may be incorporated into the formulation as well, e.g., excipients, surfactants, preservatives (e.g., antioxidants), stabilizers, chelating agents, and the like, as will be appreciated by those skilled in the art of pharmaceutical formulation preparation and drug delivery.

In another aspect of the invention, a packaged kit is provided for a patient to use in the treatment of premature ejaculation. The kit includes a pharmaceutical formulation of a phosphodiesterase inhibitor, a container housing the pharmaceutical formulation during storage and prior to administration, and instructions, e.g., written instructions on a package insert or label, for carrying out drug administration in a manner effective to treat premature ejaculation. The pharmaceutical formulation may be any formulation described herein, e.g., an oral dosage form containing a unit dosage of the phosphodiesterase inhibitor, the unit dosage being a therapeutically effective dosage for treatment of premature ejaculation.

DETAILED DESCRIPTION OF THE INVENTION

I. Definitions and Overview

Before describing the present invention in detail, it is to be understood that this invention is not limited to specific active agents, dosage forms, dosing regimens, or the like, as such may vary. It is also to be understood that the terminology used herein is for the purpose of describing particular embodiments only, and is not intended to be limiting.

It must be noted that as used in this specification and the appended claims, the singular forms "a," "an" and "the" include plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

In describing and claiming the present invention, the following terminology will be used in accordance with the definitions set out below.

The terms "active agent" and "pharmacologically active agent" are used interchangeably herein to refer to a chemical compound that induces a desired effect, i.e., in this case, treatment of premature ejaculation. The primary active agents herein are phosphodiesterase inhibitors, although combination therapy wherein a phosphodiesterase inhibitor is administered with one or more additional active agents is also within the scope of the present invention. Such combination therapy may be carried out by administration of the different active agents in a single composition, by concurrent administration of the different active agents in different compositions, or by sequential administration of the different active agents. Included are derivatives and analogs of those compounds or classes of compounds specifically mentioned that also induce the desired effect.

The term "phosphodiesterase inhibitor" as used herein is intended to mean an agent that is capable of inhibiting or reducing—selectively or nonselectively—the activity of a phosphodiesterase. Unless otherwise indicated, the term "phosphodiesterase inhibitor" is intended to include phosphodiesterase inhibitors per se as well as salts, esters, amides, prodrugs, active metabolites and other derivatives thereof, it being understood that any salts, esters, amides, prodrugs, active metabolites or other derivatives are pharmaceutically acceptable as well as pharmacologically active. Phosphodiesterase inhibitors that may be used in conjunction with the present method of treating premature ejaculation include, but are not limited to, inhibitors of the type III phosphodiesterases (i.e., the cAMP-specific-cGMP inhibitable phosphodiesterases), the type IV phospodiesterases (i.e., the high affinity-high specificity cAMP phosphodiesterases) and the Type V phosphodiesterases (cGMP-specific phosphodiesterases). Additional inhibitors that may be used in conjunction with the present invention are nonspecific phosphodiesterase inhibitors, inhibitors of cGMP-specific phosphodiesterases other than Type V phosphodiesterase, and specific and nonspecific inhibitors of any other phosphodiesterase inhibitors that are known or hereafter identified.

The terms "treating" and "treatment" as used herein refer to the ability to increase an individual's ejaculatory latency (i.e., delay ejaculation) during sexual activity, particularly sexual intercourse, relative to that individual's ejaculatory latency in the absence of pharmacotherapy as provided herein. Preferably, upon treatment according to the present invention, an individual's ejaculatory latency is increased by at least a factor of two, more preferably a factor of four and most preferably a factor of at least ten.

By an "effective" amount or a "therapeutically effective amount" of a drug or pharmacologically active agent is meant a nontoxic but sufficient amount of the drug or agent to provide the desired effect, i.e., an increase in ejaculatory latency as explained above.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well, i.e., therapeutically effective for the treatment of premature ejaculation.

By "as-needed" dosing, also referred to as "pro re nata" dosing, "prn" dosing, and "on demand" dosing or administration, is meant the administration of an active agent at some time prior to anticipated sexual activity and within a time interval sufficient to provide for the desired therapeutic effect, i.e., delay in ejaculation latency during sexual activity. Preferably, "as-needed" administration herein does not involve priming doses or chronic administration. As-needed administration may involve administration immediately prior to sexual activity, but will generally be in the range of about 0.5 to 24 hours prior to anticipated sexual activity, preferably in the range of about 1 to 12 hours prior to anticipated sexual activity, most preferably in the range of about 1 to 4 hours prior to anticipated sexual activity. "As-needed" administration will generally not involve dosing more than once a day.

The term "controlled release" is intended to refer to any drug-containing formulation in which release of the drug is not immediate, i.e., with a "controlled release" formulation, oral administration does not result in immediate release of the drug into an absorption pool. The term is used interchangeably with "nonimmediate release" as defined in *Remington: The Science and Practice of Pharmacy, Nineteenth Ed.* (Easton, Pa.: Mack Publishing Company, 1995). As discussed therein, immediate and nonimmediate release can be defined kinetically by reference to the following equation:

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area. The term "controlled release" as used herein includes any nonimmediate release formulation, including but not limited to sustained release, delayed release and pulsatile release formulations.

The term "sustained release" is used in its conventional sense to refer to a drug formulation that provides for gradual release of a drug over an extended period of time, and that preferably, although not necessarily, results in substantially constant blood levels of a drug over an extended time period.

By the term "transdermal" drug delivery is meant delivery by passage of a drug through the skin or mucosal tissue and into the bloodstream. "Transdermal" delivery is also intended to encompass passage through scrotal skin.

The term "topical administration" is used in its conventional sense to mean delivery of a topical drug or pharmacologically active agent to the skin or mucosa.

By "transmucosal" drug delivery is meant administration of a drug to the mucosal surface of an individual so that the drug passes through the mucosal tissue and into the individual's blood stream. Transmucosal drug delivery may be "buccal" or "transbuccal," referring to delivery of a drug by passage through an individual's buccal mucosa and into the bloodstream. Another form of transmucosal drug delivery herein is "sublingual" drug delivery, which refers to delivery of a drug by passage of a drug through an individual's sublingual mucosa and into the bloodstream. An additional form of transmucosal drug delivery herein is "rectal" or "transrectal" drug delivery, referring to delivery of a drug by passage of a drug through an individual's rectal mucosa and into the bloodstream. Another form of transmucosal drug delivery is "urethral" or "transurethral" delivery, referring to delivery of the drug into the urethra such that the drug contacts and passes through the wall of the urethra.

In order to carry out the method of the invention, a selected phosphodiesterase inhibitor is administered to a male individual suffering from or prone to premature ejaculation, either chronic, lifelong ("primary") premature ejaculation or acquired ("secondary") premature ejaculation. The active agent may be administered orally, transmucosally (including buccally, sublingually, transurethrally, and rectally), topically, transdermally, by inhalation, or using any other route of administration. Oral administration, because of its convenience, is preferred for those active agents that have sufficient oral bioavailability.

II. Active Agents

The active agent administered using the method of the invention is a phosphodiesterase inhibitor. The agent may be an inhibitor of a Type III phosphodiesterase, a Type IV phosphodiesterase, Type V phosphodiesterase, and/or another phosphodiesterase. Further, the agent may be a specific or a nonspecific inhibitor.

Suitable Type III inhibitors include, but are not limited to, those described in U.S. Pat. No. 6,156,753 to Doherty, Jr. et al., assigned to VIVUS, Inc. (Mountain View, Calif.). Such inhibitors include, by way of example: bipyridines such as milrinone, amrinone and olprinone; imidazolones such as piroximone and enoximone; imidazolines such as imazodan and 5-methyl-imazodan; imidazoquinoxalines; dihydropyridazinones such as indolidan and LY181512 (5-(6-oxo-1, 4,5,6-tetrahydro-pyridazin-3-yl)-1,3-dihydro-indol-2-one); dihydroquinolinone compounds such as cilostamide, cilostazol, vesnarinone, and OPC 3911 (N-cyclohexyl-N-hydroxymethyl-4-(2-oxo-1,2-dihydro-quinolin-6-yloxy)-butyramide); other compounds such as anagrelide, bemoradan, ibudilast, isomazole, lixazinone, motapizone, olprinone, phthalazinol, pimobendan, quazinone, siguazodan and trequinsin; and mixed Type III and Type IV inhibitors such as benafentrine, cis-6-[p-acetamidophenyl]-1,2,3,4,4a, 10 b-hexahydro-8,9-dimethoxy-2-methylbenzo-[c][1,6]-naphthyridine, EMD 54622 (5-[1-(3,4-dimethoxybenzoyl)-4,4-dimethyl-1,2,3,4-tetrahydrochinolin-6-yl]-6-methyl-3,6-dihydro-1,3,4-thiadiazin-2-one), Org 20241 (N-hydroxy-4-[3,4-dimethoxyphenyl]-thiazole-2-carboximidamide), Org30029 (N-hydroxy-5,6-dimethoxybenzo-[b]-thiophene-2-carboximidamide), saterinone, tolafentrine and zardaverine.

Suitable Type IV inhibitors include, but are not limited to, those described in U.S. Pat. No. 6,127,363 to Doherty, Jr. et al., also assigned to VIVUS, Inc. Examples of Type IV inhibitors that can be administered in conjunction with the present method include, by way of example: pyrrolidinones such as rolipram (4-(3-cyclopentyloxy-4'-methoxyphenyl)-2-pyrrolidinone)) and rolipram derivatives such as RO20-1724 (4-(3-butyloxy-4-methoxyphenyl)-imidazolidinone) and RS 33793 (8-(3-nitrophenyl)-6-(3-methyl-2-butenyl) pyrido-[2,3a]pyrazin-5-one); quinazolinediones such as nitraquazone (3-[3'-nitrophenyl]N-ethylquinazoline-2,6-dione), CP-77059 (1-(carbomethoxyphenyl)-3-benzyl-pyrido[2,3d]pyrimidine-2,4(1H,3H)dione), RS-25344 (1-(3-nitrophenyl)-3-(4-pyridylmethyl)-1,2,3,4-tetrahydro pyrido (2,3-d) pyrimidine-2,4-dione)) and other nitraquazone analogs; xanthine derivatives such as denbufylline (1,3-di-n-butyl-7-[2'-oxopropyl]xanthine), XT-44 (1-n-butyl-3-n-propylxanthine), arofylline (LAS 31025; 1-propyl-3-(4-chlorophenyl)-xanthine) and BRL 61063; phenyl ethyl pyridines such as CDP 840 (4-(1-(3-cyclopentyloxy-4-methoxyphenyl)-2-phenylethyl) pyridine) and compounds disclosed in WO 97/22585 to Guay et al.; tetrahydropyrimidones such as atizoram (CP 80633); diazepine derivatives such as CI 1018 and compounds disclosed in WO 97/36905 to Pascal et al.; oxime carbamates such as filaminast (PDA-641); naphthyridinones such as RS 17597; benzofurans such as 2-butyl-7-methoxy-benzofuran-4-carboxylic acid (3,5-dichloropyridin-4yl)-amide, 2-benzyl-7-methoxy-benzofuran-4-carboxylic acid (3,5-dichloropyridin-4-yl)-amide, 7-methoxy-2-phenethyl-benzofuran-4-carboxylic acid (3,5-dichloropyridin-4-yl)-amide and 5-(2-butyl-7-methoxy-benzofuran-4-yl)-tetrahydro-pyrimidin-2-one, phenanthridines, such as those disclosed in U.S. Pat. No. 6,191,138 to Gutterer; 2-heteroaryl and 2-heterocyclic benzoxazoles, such as those disclosed in U.S. Pat. No. 6,166,041 to Cavalla et al.; phenyldihydro-benzofurane compounds such as those disclosed in U.S. Pat. No. 5,902,824 to Ulrich; benzofuran carboxamides as disclosed in U.S. Pat. No. 6,211,203 to Amschler et al.; 4-substituted benzofurane compounds such as those disclosed in EP 819688A1; substituted furans as disclosed in Perrier et al. (1999) *Bioorg. Med. Chem. Lett.* 9:323–326 (1999); naphthalene derivatives such as T 440; purine derivatives such as V 112294A and those compounds disclosed in U. S. Pat. No. 6,228,859 to Cavalla et al.; cyclohexane carboxylic acids such as ariflo (SB 207499, c-4-cyano-4-[3'-cyclopentyloxy4'-methoxyphenyl]-r-1-cyclohexane-carboxylic acid); benzamides such as piclamilast (RP73401; N-(3,5-dichloro-4-pyridyl)-3-cyclopentoxy-4-methoxybenzamide); benzothiophenes such as tibenelast (LY 186655); pyridopyridazinones such as 8-(3-nitrophenyl)-6-pyridin-4-ylmethyl-6H-pyrido[2,3-d] pyridazin-5-one; imidazolidinones such as 5-[3-bicyclo [2.2.1]hept-2-yloxy)-4-methoxyphenyl-1-methyl-imidazolidin-2-one; substituted phenyl compounds, as disclosed in U.S. Pat. No. 5,891,896 to Warrellow et al.; substituted biphenyl compounds as disclosed in U.S. Pat. No. 5,877,190 to Dhainaut et al.; etazolate; and S-(+)-glaucine ((S)-(+)-1,2,9,10-tetramethoxy-aporphine).

Examples of type V phosphodiesterase inhibitors include, but are not limited to, the pyrazolopyrimidinones such as those disclosed in PCT Publication No. WO 94/28902, and the griseolic acid derivatives, 2-phenylpurinone derivatives, phenylpyridone derivatives, fused and condensed pyrimidines, pyrimidopyrimidine derivatives, purine compounds, quinazoline compounds, phenylpyrimidinone derivative, imidazoquinoxalinone derivatives, and other compounds disclosed in WO 96/16644.

Suitable pyrazolopyrimidinones, as disclosed in WO 94/28902, are 5-(2-ethoxy-5-morpholinoacetylphenyl)-1-methyl-3-n-propyl-1,6-dihydro-7H-pyrazolo[4,3d] pyrimidin-7-one, 5-(5-morpholinoacetyl-2-n-propoxyphenyl)-1-methyl-3-n-propyl-1,6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d] pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonyl)phenyl]-1-methyl-3-n-propyl-1,6-dihydro-7H-pyrazolo [4,3-d] pyrimidin-7-one, 5-[5-[4-(2-hydroxyethyl)-1-piperazinylsulfonyl]-2-n-propoxyphenyl]-1-methyl 1,3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d] pyrimidin-7-one and 5-[2-ethoxy-5-(1-methyl-2-imidazolyl) phenyl]-1-methyl-3-n-propyl-1,6-dihydro-7H-pyrazolo[4,3-d]pyrimidin-7-one.

The griseolic acid derivatives, 2-phenylpurinones, etc. disclosed in WO 96/16644 include 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid-4(3H)-one, 7-methylthio-4-oxo-2-(2-propoxyphenyl)-3,4-dihydro-pyrimido[4,5-d]pyrimidine, 6-hydroxy-2-(2-propoxyphenyl)pyrimidine-4-carboxamide, 1-ethyl-3-methylimidazo[1,5a]quinoxalin-4(5H)-one, 4-phenylmethylamino-6-chloro-2-(1-imidazoloyl) quinazoline, 5-ethyl-8-[3-(N-cyclohexyl-N-methylcarbamoyl)-propyloxy]-4,5-dihydro-4-oxo-pyrido[3,2-e]-pyrrolo[1,2-a]pyrazine, 5'-methyl-3'-(phenylmethyl)-spiro[cyclopentane-1,7'(8'H)-(3'H)-imidazo[2,1-b]purin]4' (5'H)-one, 1-[6-chloro-4-(3,4-methylenedioxybenzyl)-aminoquinazolin-2-yl)piperidine-4-carboxylic acid, (6R, 9S)-2-(4-trifluoromethyl-phenyl)methyl-5-methyl-3,4,5,6a,7,8,9,9a-octa hydrocyclopent[4,5]-imidazo[2,1-b]-purin-4-one, 1-t-butyl-3-phenylmethyl-6-(4-pyridyl)pyrazolo[3,4-d]-pyrimid-4-one, 1-cyclopentyl-3-methyl-6-(4-pyridyl)-4,5-dihydro-1H-pyrazolo[3,4-d]pyrimid-4-one, 2-butyl-1-(2-chlorobenzyl)6-ethoxy-carbonylbenzimidaole, 2-(4-carboxy-piperidino)--4-(3,4-methylenedioxy-benzyl) amino-6-nitroquinazoline and 2-phenyl-8-ethoxycycloheptimidazole.

Still other type V phosphodiesterase inhibitors useful in conjunction with the method of the present invention include: those compounds described in PCT Publication No. WO 01/19802 to Aoyama (Tanabe Seiyaku Co., Ltd.), particularly (S)-2-(2-hydroxymethyl-1-pyrrolidinyl)-4-(3-chloro-4-methoxy-benzylamino)-5-[N-(2-pyrimidinylmethyl)carbamoyl]pyrimidine, 2-(5,6,7,8-tetrahydro-1,7-naphthyridin-7-yl)-4-(3-chloro-4-methoxybenzylamino)-5-[N-(2-morpholinoethyl) carbamoyl]-pyrimidine, and (S)-2-(2-hydroxymethyl-1-pyrrolidinyl)-4-(3-chloro-4-methoxy-benzylamino)-5-[N-(1,3,5-trimethyl-4-pyrazolyl)carbamoyl]pyrimidine; zaprinast (1,4-dihydro-5-(2-propoxyphenyl)-7H-1,2,3-triazolo[4,5-d]pyrimidin-7-one); 1-(3-chloroanilino)-4-phenylphthalazine (MY5445); dipyridamole, vinpocetine; FR229934 (Fujisawa Pharmaceutical Co., Ltd.); 1-methyl-3-isobutyl-8-(methylamino)xanthine; IC-351 (Cialis®); 4-aryl-1-isoquinolinone derivatives such as methyl 2-(4- aminophenyl)-1,2-dihydro-1-oxo-7-(2-pyridinylmethoxy)-4-(3,4,5-trimethoxyphenyl)-3-isoquinoline carboxylate dihydrochloride and the sulfate salt thereof (T-1032); 4-bromo-5-(pyridylmethylamino)-6-[3-(4-chlorophenyl) propoxy]-3(2H)pyridazinone; 1-[4-[(1,3-benzodioxol-5-ylmethyl)amino]-6-chloro-2-quinazolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]imidazo[2,1-b]purin-4-one; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidine carboxylic acid, monosodium salt; Pharmaprojects No. 4516 (Glaxo Wellcome); vardenafil (Bayer); Pharmaprojects No. 5064 (Kyowa Hakko; see WO 96/26940); Pharmaprojects No. 5069 (Schering Plough); GF-196960 (Glaxo Wellcome); Sch-51866; sodium 1-[6-chloro-4-(3,4-methylenedioxybenzyl)-aminoquinazolin-2-yl]piperidine-4-carboxylate sesquihydrate (E4021); and 6-phenylpyrazolo[3,4-d]pyrimidinones such as 1,3-dimethyl-6(2-propoxy-5-methanesulfonamidophenyl)-1,5-dihydropyrazolo[3,4-d]pyrimidin-4-one and 1-ethyl-3-methyl-6-(2-propoxy-5-(4-methylthiazol-2-yl)phenyl-1,5-dihydropyrazolo[3,4-d]pyrimidin-4-one.

Particularly preferred Type V phosphodiesterase inhibitors for use in conjunction with the present invention are sildenafil (5-[2-ethoxy-5-(4-methyl-1-piperazinylsulphonyl)phenyl]-1-methyl-3-n-propyl-1,6-dihydro-7H-pyrazolo[4,3-dipyrimidin-7-one]), zaprinast, dipyridamole, and the compounds described in WO 01/19802 to Aoyama, particularly (S)-2-(2-hydroxymethyl-1-pyrrolidinyl)-4-(3-chloro-4-methoxy-benzylamino)-5-[N-(2-pyrimidinylmethyl)carbamoyl]pyrimidine, 2-(5,6,7,8-tetrahydro-1,7-naphthyridin-7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxy-benzylamino)-5-[N-(1,3,5-trimethyl-4-pyrazolyl)carbamoyl]pyrimidine, and pharmaceutically acceptable salts thereof. Sildenafil, preferably in the form of an acid addition salt (e.g., sildenafil citrate), is most preferred.

Other phosphodiesterase inhibitors include nonspecific inhibitors such as theophylline, theobromine, IBMX, pentoxifylline and papaverine.

One or more additional active agents can be administered with the phosphodiesterase inhibitor, either simultaneously or sequentially. The additional active agent will generally although not necessarily be one that is effective in treating premature ejaculation, and/or an agent that potentiates the effect of the phosphodiesterase inhibitor. Suitable secondary agents include, for example, those described in U.S. Pat. No. 6,228,864 to Smith et al., assigned to VIVUS, Inc. (Mountain View, Calif.), i.e.:

antidepressant drugs such as amesergide, amineptine, amitriptyline, amoxapine, benactyzine, brofaromine, bupropion, butriptyline, cianopramine, citalopram, clomipramine, clorgyline, clovoxamine, dapoxetine, demexiptiline, desipramine, dibenzepin, dimetacrine, dothiepin, doxepin, duloxetine, etoperidone, femoxetine, fezolamine, fluoxetine, fluvoxamine, ifoxetine, imipramine, iprindole, isocarboxazid, levoprotiline, lofepramine, maprotiline, medifoxamine, melitracen, metapramine, methylphenidate, mianserin, milnacipran, minaprine, mirtazapine, moclobemide, nefazodone, nialamide, nomifensine, nortriptyline, opipramol, oxaflozane, oxaprotiline, oxitriptan, paroxetine, phenelzine, pirlindole, propizepine, protriptyline, quinupramine, rolipram, selegiline, sertraline, setiptiline, sibutramine, teniloxazine, tianeptine, tofenacin, toloxatone, tranylcypromine, trazodone, trimipramine, tryptophan, venlafaxine, viloxazine, viqualine and zimeldine;

serotonin agonists such as 2-methyl serotonin, buspirone, ipsaperone, tiaspirone, gepirone, 8-hydroxy-(2-N,N-dipropylamino)-tetraline, 1-(4-bromo-2,5-dimethoxyphenyl)-2-aminopropane, cisapride, sumatriptan, m-chlorophenyl-piperazine, trazodone, zacopride and mezacopride;

serotonin antagonists such as ondansetron, granisetron, metoclopramide, tropisetron, dolasetron, palonosetron, trimethobenzamide, methysergide, risperidone, ketanserin, ritanserin, clozapine, amitriptyline, MDL 100,907, azatadine, cyproheptadine, fenclonine, chlorpromazine, mianserin, zacopride and mezacopride;

adrenergic agonists including methoxamine, methpentermine, metaraminol, mitodrine, clonidine, apraclonidine, guanfacine, guanabenz, methyldopa, amphetamine, methamphetamine, epinephrine, norepinephrine, ethylnorepinephrine, phenylephrine, ephedrine, pseudoephedrine, methylphenidate, pemoline, naphazoline, tetrahydrozoline, oxymetazoline, xylometazoline, phenylpropanolamine, phenylethylamine, dopamine, dobutamine, colterol, isoproterenol, isotharine, metaproterenol, terbutaline, metaraminol, tyramine, hydroxyamphetamine, ritodrine, prenalterol, albuterol, isoetharine, pirbuterol, bitolterol, fenoterol, formoterol, procaterol, salmeterol, mephenterine and propylhexedrine;

adrenergic neurone blockers including bethanidine, debrisoquine, guabenxan, guanadrel, guanazodine, guanethidine, guanoclor and guanoxan; and adrenergic antagonists including phenoxybenzamine, phentolamine, tolazoline, prazosin, terazosin, doxazosin, trimazosin, yohimbine, ergot alkaloids, labetalol, ketanserin, urapidil, alfuzosin, bunazosin, tamsulosin, chlorpromazine, haloperidol, phenothiazines, butyrophenones, propranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone and indoramin.

Some of these additional active agents, as may be seen, are encompassed by more than one of the above categories, e.g., serotonin antagonists and antidepressants, or serotonin agonists and antagonists.

Preferred additional active agents are 5-HT$_3$ antagonists and 5-HT$_4$ agonists. 5-HT$_3$ receptors can be found, for example, on parasympathetic terminals in the gastrointestinal tract and in the central nervous system, both of which participate in the emetic response. 5-HT$_4$ receptors are found throughout the body, including on nerve terminals in the CNS, the gastrointestinal tract, and on smooth muscle and secretory cells. 5-HT$_4$ receptors activate adenylyl cyclase, and are involved in the regulation of secretion and peristalsis. Examples of 5-HT$_3$ antagonists include, without limitation, ondansetron, ergot alkaloids, granisetron, metoclopramide, trimethobenzamide, tropisetron, dolasetron, batanopride and zacopride. Exemplary 5-HT$_4$ agonists include, but are not limited to, the following: N-(3-hydroxy-4-piperidenyl) benzamides such as cisapride (cis-4-amino-5-chloro-N-[1-[3-(4-fluorophenoxy)propyl]-3-methoxy-4-piperidinyl]-2-methoxybenzamide) and norcisapride (4-amino-5-chloro-N-(3-methoxy-4-piperidinyl)-2 methoxybenzamide), as racemates or in isomerically pure form; indazolecarboxamides, as described in U.S. Pat. No. 5,817,676, and 1-phenylalkanones, as described in U.S. Pat. No. 5,763,458. Cisapride and norcisapride, whether racemic or optically pure, are preferred 5-HT$_4$ agonists.

Other preferred additional active agents are antidepressant drugs classified as selective serotonin reuptake inhibitors (SSRIs). These include, by way of example, amitryptyline, clomipramine, citalopram, dapoxetine, desipramine, doxepin, duloxetine, fluoxetine, fluvoxamine, imipramine, isocarboxazid, mirtazapine, nortriptyline, paroxetine, phenelzine, protriptyline, nefazodone, selegiline, sertraline, tranylcypromine, trazodone, trimipramine and venlafaxine. By virtue of combining such agents with phosphodiesterase inhibitors, the dosage of an SSRI that will be effective in treating premature ejaculation may be substantially reduced, in turn minimizing those side effects that commonly result from SSRI administration.

Other additional active agents that may be co-administered with the phosphodiesterase inhibitor, but are less preferred, are disclosed in U.S. Pat. No. 6,228,864 to Smith et al., and include vasoactive agents such as: nitrates and like compounds such as nitroglycerin, isosorbide dinitrate, erythrityl tetranitrate, amyl nitrate, sodium nitroprusside, molsidomine, linsidomine chlorhydrate ("SIN-1"), S-nitroso-N-acetyl-d,1-penicillamine ("SNAP"), S-nitroso-N-cysteine and S-nitroso-N-glutathione ("SNO-GLU") and diazenium diolates ("NONOates"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; Rec15/2739; trazodone; naturally occurring prostaglandins such as PGE$_0$, PGE$_1$, PGA$_1$, PGB$_1$, PGF$_{1\alpha}$, 19-hydroxy-PGA$_1$, 19-hydroxy-PGB$_1$, PGE$_2$, PGA$_2$, PGB$_2$, 19-hydroxy-PGA$_2$, 19-hydroxy-PGB$_2$, PGE$_3$, PGF$_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptide.

Any of the active agents may be administered in the form of a salt, ester, amide, prodrug, active metabolite, derivative, or the like, provided that the salt, ester, amide, prodrug or derivative is suitable pharmacologically, i.e., effective in the present method. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts are prepared from the free base using conventional methodology, and involves reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Particularly preferred acid addition salts of the active agents herein are salts prepared with organic acids. Conversely, preparation of basic salts of acid moieties which may be present on an active agent are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Amides and prodrugs may also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety, which results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

III. Pharmaceutical Compositions and Dosage Forms

Suitable compositions and dosage forms include tablets, capsules, caplets, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, and the like.

A. Oral Dosage Forms:

Oral dosage forms are preferred for those therapeutic agents that are orally active, and include tablets, capsules, caplets, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, 20$^{th}$ Edition, Gennaro, A. R., Ed. (Lippincott, Williams and Wilkins, 2000). Tablets and capsules represent the most convenient oral dosage forms, in which case solid pharmaceutical carriers are employed.

Tablets may be manufactured using standard tablet processing procedures and equipment. One method for forming tablets is by direct compression of a powdered, crystalline or granular composition containing the active agent(s), alone or in combination with one or more carriers, additives, or the like. As an alternative to direct compression, tablets can be prepared using wet-granulation or dry-granulation processes. Tablets may also be molded rather than compressed, starting with a moist or otherwise tractable material; however, compression and granulation techniques are preferred.

In addition to the active agent(s), then, tablets prepared for oral administration using the method of the invention will generally contain other materials such as binders, diluents, lubricants, disintegrants, fillers, stabilizers, surfactants, coloring agents, and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, magnesium stearate, calcium stearate, and stearic acid. Stearates, if present, preferably represent at no more than approximately 2 wt. % of the drug-containing core. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

The dosage form may also be a capsule, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy,* cited supra, which describes materials and methods for preparing encapsulated pharmaceuticals. If the active agent-containing composition is present within the capsule in liquid form, a liquid carrier is necessary to dissolve the active agent(s). The carrier must be compatible with the capsule material and all components of the pharmaceutical composition, and must be suitable for ingestion.

Solid dosage forms, whether tablets, capsules, caplets, or particulates, may, if desired, be coated so as to provide for delayed release. Dosage forms with delayed release coatings may be manufactured using standard coating procedures and equipment. Such procedures are known to those skilled in the art and described in the pertinent texts, e.g., in *Remington,* supra. Generally, after preparation of the solid dosage form, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained release dosage forms provide for drug release over an extended time period, and may or may not be delayed release. Generally, as will be appreciated by those of ordinary skill in the art, sustained release dosage forms are formulated by dispersing a drug within a matrix of a gradually bioerodible (hydrolyzable) material such as an insoluble plastic, a hydrophilic polymer, or a fatty compound, or by coating a solid, drug-containing dosage form with such a material. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

B. Transmucosal Compositions and Dosage Forms:

Although the present compositions will generally be administered orally, other modes of administration are suitable as well. For example, transmucosal administration may be advantageously employed. Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Preferred buccal dosage forms will typically comprise a therapeutically effective amount of the selected phosphodiesterase inhibitor and a bioerodible (hydrolyzable) polymeric carrier that may also serve to adhere the dosage form to the buccal mucosa. The buccal dosage unit is fabricated so as to erode gradually over a predetermined time period, wherein drug delivery is provided essentially throughout. The time period is typically in the range of approximately 0.5 hours to 24 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. The "therapeutically effective amount" of phosphodiesterase inhibitor in the dosage unit will of course depend on the potency of the agent and the intended dosage, which, in turn, is dependent on the particular individual undergoing treatment, the specific indication, and the like. The dosage unit will generally contain from approximately 1.0 wt. % to about 60 wt. % active agent, preferably on the order of 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the phosphodiesterase inhibitor to be administered and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Preferred sublingual dosage forms include sublingual tablets, creams, ointments and pastes. The tablet, cream, ointment or paste for sublingual delivery comprises a therapeutically effective amount of the selected phosphodiesterase inhibitor and one or more conventional nontoxic carriers suitable for sublingual drug administration. The sublingual dosage forms of the present invention can be manufactured using conventional processes. The sublingual dosage unit is fabricated to disintegrate rapidly. The time period for complete disintegration of the dosage unit is typically in the range of from about 10 seconds to about 30 minutes, and optimally is less than 5 minutes.

Other components may also be incorporated into the sublingual dosage forms described herein. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual dosage forms are known, or will be apparent, to those skilled in this art; for example, see *Remington: The Science and Practice of Pharmacy,* cited supra.

For transurethral administration, the formulation comprises a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the particular phosphodiesterase inhibitor administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), surfactants as discussed above, including, for example, Tergitol®, Nonoxynol-9® and TWEEN-80®, and lower alkanols such as ethanol.

Figure 1:
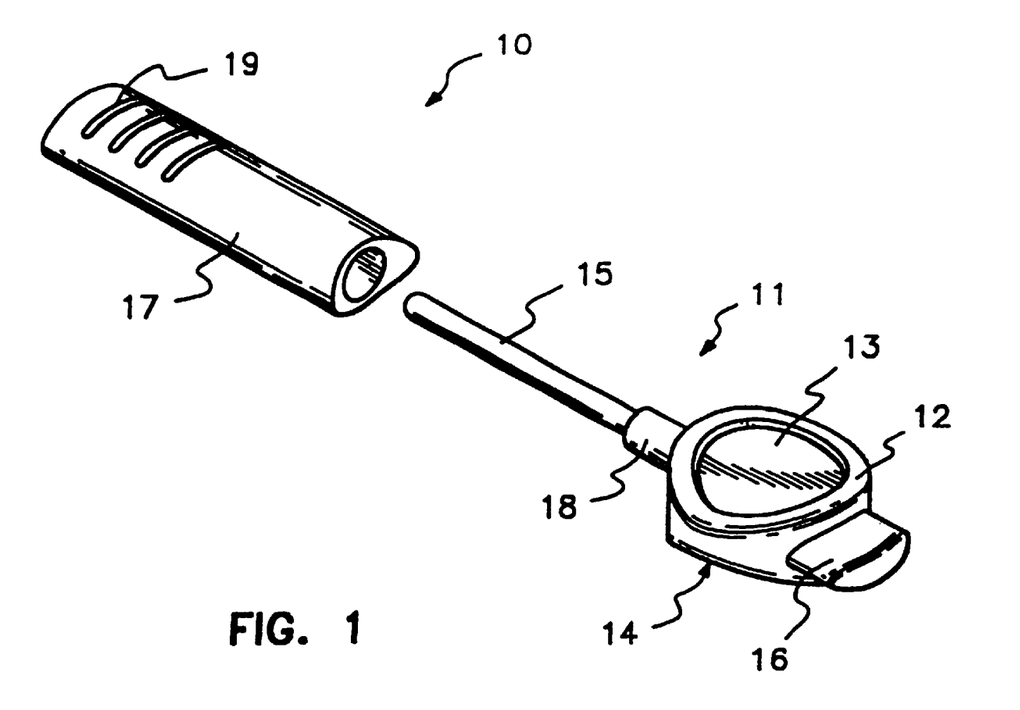
FIG. 1 is an exploded, perspective view of one embodiment of a transurethral drug administration device that may be used in conjunction with the present method.

Transurethral drug administration, as explained in U.S. Pat. Nos. 5,242,391, 5,474,535, 5,686,093 and 5,773,020 to Place et al., can be carried out in a number of different ways using a variety of urethral dosage forms. For example, the drug can be introduced into the urethra from a flexible tube, squeeze bottle, pump or aerosol spray. The drug may also be contained in coatings, pellets or suppositories that are absorbed, melted or bioeroded in the urethra In certain embodiments, the drug is included in a coating on the exterior surface of a penile insert. A preferred drug delivery device for administering a drug transurethrally is shown in FIG. 1. It is preferred, although not essential, that the drug be delivered at least about 3 cm into the urethra, and preferably at least about 7 cm into the urethra. Generally, delivery at about 3 cm to about 8 cm into the urethra will provide effective results in conjunction with the present method.

Urethral suppository formulations containing PEG or a PEG derivative are particularly preferred urethral dosage forms herein, and may be conveniently formulated using conventional techniques, e.g., compression molding, heat molding or the like, as will be appreciated by those skilled in the art and as described in the pertinent literature and pharmaceutical texts. See, for example, *Remington: The Science and Practice of Pharmacy,* cited supra, which discloses typical methods of preparing pharmaceutical compositions in the form of urethral suppositories. The PEG or PEG derivative preferably has a molecular weight $M_w$ in the range of about 200 to 2500, more preferably in the range of about 1000 to 2000. Suitable polyethylene glycol derivatives include polyethylene glycol fatty acid esters, for example, polyethylene glycol monostearate, polyethylene glycol sorbitan esters, e.g., polysorbates, and the like. Depending on the particular active agent, it may also be preferred that urethral suppositories contain one or more solubilizing agents effective to increase the solubility of the active agent in the PEG or other transurethral vehicle.

It may be desirable to deliver the active agent in a urethral dosage form that provides for controlled or sustained release of the agent. In such a case, the dosage form comprises a biocompatible, biodegradable material, typically a biodegradable polymer. Examples of such polymers include polyesters, polyalkylcyanoacrylates, polyorthoesters, polyanhydrides, albumin, gelatin and starch. As explained, for example, in PCT Publication No. WO96/40054, these and other polymers can be used to provide biodegradable microparticles that enable controlled and sustained drug release, in turn minimizing the required dosing frequency.

The urethral dosage form will preferably comprise a suppository that is on the order of 2 to 20 mm, preferably 5 to 10 mm, in length and less than about 5 mm, preferably less than about 2 mm in width. The weight of the suppository will typically be in the range of approximately 1 mg to 100 mg, preferably in the range of approximately 1 mg to 50 mg. However, it will be appreciated by those skilled in the art that the size of the suppository can and will vary, depending on the potency of the drug, the nature of the formulation, and other factors.

In FIG. 1, a suitable transurethral drug delivery device is shown generally at 10. The device comprises a transurethral inserter 11 having an easily graspable segment 12 that has opposing symmetrically concave surfaces 13 and 14 adapted to be held by two fingers. Drug is contained within a urethral suppository (not shown) within shaft 15, which is sized to fit within the urethra. A longitudinal plunger, the tip of which is seen at 16, is slidably insertable into the longitudinal bore contained within shaft 15. To extrude drug into the urethra, shaft 15 is inserted into the urethra, and plunger tip 16 is pushed into segment 12. The inserter 11 is then removed. Prior to use, and during storage, the device is capped with elongate cap 17 which fits snugly over flange 18 at the proximal end of shaft 15. The cap 17 is provided with a series of parallel ridges 19 to facilitate gripping of the cap and removal from inserter 11.

Although the transurethral drug delivery device shown in FIG. 1 represents a preferred device for use herein, again, it should be emphasized that a wide variety of device configurations and urethral dosage forms can be used.

Transurethral drug delivery may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO96/40054, cited above. Briefly, the active agent is driven through the urethral wall by means of an electric current passed from an external electrode to a second electrode contained within or affixed to a urethral probe.

Preferred transrectal dosage forms include rectal suppositories, creams, ointments, and liquid formulations (enemas). The suppository, cream, ointment or liquid formulation for transrectal delivery comprises a therapeutically effective amount of the selected phosphodiesterase inhibitor and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration is preferably in the range of from about 10 minutes to about 6 hours, and optimally is less than 3 hours.

Other components may also be incorporated into the transrectal dosage forms described herein. The additional components include, but are not limited to, stiffening agents, antioxidants, preservatives, and the like. Examples of stiffening agents that may be used include, for example, paraffin, white wax and yellow wax. Preferred antioxidants, if used, include sodium bisulfite and sodium metabisulfite.

The active agents may also be administered intranasally or by inhalation. Compositions for nasal administration are generally liquid formulations for administration as a spray or in the form of drops, although powder formulations for intranasal administration, e.g., insufflations, are also known. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation may take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation may also comprise dry powder formulations, particularly insufflations in which the powder has an average particle size of about 0.1 $\mu$m to 50 $\mu$m, preferably 1 $\mu$m to about 25 $\mu$m.

C. Topical Formualtions:

Topical formulations may be in any form suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy,* supra, at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, see *Remington: The Science and Practice of Pharmacy* for further information.

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels-are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are described in part (B) of this section.

D. Transdermal Administration:

The compounds of the invention may also be administered through the skin or mucosal tissue using conventional transdermal drug delivery systems, wherein the agent is contained within a laminated structure (typically referred to as a transdermal "patch") that serves as a drug delivery device to be affixed to the skin. Transdermal drug delivery may involve passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present, the backing is preferably made of a sheet or film of a flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well know in the art and include, for example, those enhancers listed above in part (B) of this section.

E. Parenteral Administration:

Parenteral administration, if used, is generally characterized by injection, including intramuscular, intraperitoneal, intravenous (IV) and subcutaneous injection. Injectable formulations can be prepared in conventional forms, either as liquid solutions or suspensions, solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. A more recently revised approach for parenteral administration involves use of a slow release or sustained release system; see, e.g., U.S. Pat. No. 3,710,795.

IV. Dosage and Administration

The concentration of the active agent in any of the aforementioned dosage forms and compositions can vary a great deal, and will depend on a variety of factors, including the type of composition or dosage form, the corresponding mode of administration, the nature and activity of the specific active agent, and the intended drug release profile.

Preferred dosage forms contain a unit dose of active agent, i.e., a single therapeutically effective dose. For creams, ointments, etc., a "unit dose" requires an active agent concentration that provides a unit dose in a specified quantity of the formulation to be applied. The unit dose of any particular active agent will depend, of course, on the active agent and on the mode of administration. For sildenafil citrate, the unit dose for oral administration will be in the range of about 1 mg to about 250 mg, typically in the range of about 15 mg to about 100 mg, for local administration, suitable unit doses may be lower. Those of ordinary skill in the art of pharmaceutical formulation can readily deduce suitable unit doses for other phosphodiesterase inhibitors, as well as suitable unit doses for other types of active agents that may be incorporated into a dosage form of the invention.

The amount of a particular active agent administered to a given individual will, of course, be dependent on a number of factors as well, including the specific active agent, composition or dosage form, the selected mode of administration, the age and general condition of the individual being treated, the severity of the individual's condition, and other factors known to the prescribing physician.

In a preferred embodiment, drug administration is on an as-needed basis, and does not involve chronic drug administration. With an immediate release dosage form, i.e., a composition or dosage form that is not "controlled release" as defined hereinabove, as-needed administration may involve drug administration immediately prior to sexual activity, but will generally be in the range of about 0.5 to 24 hours prior to anticipated sexual activity, preferably in the range of about 1 to 12 hours prior to anticipated sexual activity, most preferably in the range of about 1 to 4 hours prior to anticipated sexual activity. With a sustained release dosage form, a single dose can provide therapeutic efficacy over an extended time period in the range of about 4 to 48 hours, typically in the range of about 4 to 24 hours, depending on the formulation. That is, the release period may be varied by the selection and relative quantity of particular sustained release polymers; see Section III, part (A). If necessary, however, drug administration may be carried out within the context of an ongoing dosage regimen, i.e., on a weekly basis, twice weekly, daily, etc.

V. Packaged Kits

In another embodiment, a packaged kit is provided that contains the pharmaceutical formulation to be administered, i.e., a pharmaceutical formulation containing a phosphodiesterase inhibitor for the treatment of premature ejaculation, a container, preferably sealed, for housing the formulation during storage and prior to use, and instructions for carrying out drug administration in a manner effective to treat premature ejaculation. The instructions will typically be written instructions on a package insert and/or on a label. Depending on the type of formulation and the intended mode of administration, the kit may also include a device for administering the formulation (e.g., a transurethral drug delivery device such as shown in FIG. 1). The formulation may be any suitable formulation as described herein. For example, the formulation may be an oral dosage form containing a unit dosage of the phosphodiesterase inhibitor. The kit may contain multiple formulations of different dosages of the same agent. The kit may also contain multiple formulations of different active agents.

The kit may also include a venous flow control (VFC) device such as that described in U.S. Pat. No. 5,855,548 to Place, assigned to VIVUS, Inc., Mountain View, Calif. Such devices are formed from a length of flexible tubing having an integral fastening means, so as to provide for readily adjustable venous flow control when applied to the penis. The device is applied to the base of the penis prior to and during sexual intercourse, such that it effectively enhances retention of blood within the penis without substantially obstructing arterial inflow or becoming too constrictive during the erectile process. Use of the VFC device also enables enhanced effectiveness of local drug therapy, in that, for example, a transurethrally administered active agent is retained within the penis, allowing movement into the corpus cavernosa.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

EXAMPLE 1

Preparation of transmucosal paste: A transmucosal formulation is prepared containing zaprinast, a Type V phosphodiesterase inhibitor. 10 g of bulk zaprinast is placed in a mortar and a pestle is used to grind the solid into a fine powder. About 10 g of a previously weighed out quantity of 100 g of ORABASE® (Colgate-Hoyt Laboratories, Norwood, Mass.) is combined with the zaprinast powder on an ointment tile. The zaprinast powder and ORABASE® are levigated together using a spatula. The remaining ORABASE® is added to the ointment tile and levigated with the previously mixed components to produce a smooth, consistent formulation. The resulting formulation is a 10% zaprinast transmucosal formulation.

This procedure can be used with various phosphodiesterase inhibitors, ointment bases and additional components, e.g., enhancers or the like.

EXAMPLE 2

Preparation of transmucosal paste: A transmucosal formulation is prepared containing sildenafil citrate, a Type V phosphodiesterase inhibitor. About 5 g of bulk sildenafil citrate is placed in a mortar and a pestle is used to grind the solid into a fine powder. About 5 g of a previously weighed out quantity of 100 g of ORABASE® is combined with the sildenafil citrate powder on an ointment tile. The sildenafil citrate powder and ORABASE® are levigated together using a spatula. The remaining ORABASE® is added to the ointment tile and levigated with the previously mixed components to produce a smooth, consistent formulation. The resulting formulation is a 5% sildenafil citrate transmucosal formulation.

EXAMPLE 3

Preparation of buccal dosage form: 10 g of zaprinast and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of zaprinast.

EXAMPLE 4

Preparation of a buccal dosage form: 10 g of sildenafil citrate and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of sildenafil citrate.

EXAMPLE 5

Preparation of a buccal dosage form: 10 g of milrinone (a Type III phosphodiesterase inhibitor) and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of milrinone.

EXAMPLE 6

Preparation of a buccal dosage form: 10 g of rolipram (a Type IV phosphodiesterase inhibitor) and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of rolipram.

EXAMPLE 7

Preparation of a sublingual tablet: 1.0 g of zaprinast, 1.0 g of mannitol, 2.0 g of microcrystalline cellulose, and 10 mg of magnesium stearate are blended in a suitable mixer and then compressed into sublingual tablets. Each sublingual tablet contains 10 mg of zaprinast.

EXAMPLE 8

Preparation of a sublingual tablet: 1.0 g of sildenafil citrate, 1.0 g of mannitol, 2.0 g of microcrystalline cellulose, and 10 mg of magnesium stearate are blended in a suitable mixer and then compressed into sublingual tablets. Each sublingual tablet contains 10 mg of sildenafil citrate.

EXAMPLE 9

Preparation of a rectal suppository: A pharmaceutical formulation containing a Type V phosphodiesterase inhibitor for transrectal administration is prepared by mixing 10 to 100 mg zaprinast with polyethylene glycol, molecular weight approximately 4000, and heating the mixture to a temperature just high enough to produce a zaprinast-polymer melt. The zaprinast-polyethylene glycol mixture can then be poured into a mold suitable to provide a zaprinast rectal suppository, and allowed to cool. The suppository so provided is a unit dosage form suitable for transrectal administration.

EXAMPLE 10

Preparation of a rectal suppository: A pharmaceutical formulation containing an a Type V phosphodiesterase inhibitor for transrectal administration is prepared by mixing 10 to 100 mg sildenafil citrate with polyethylene glycol, molecular weight approximately 4000, and heating the mixture to a temperature just high enough to produce a sildenafil citrate-polymer melt. The sildenafil citrate-polyethylene glycol mixture can then be poured into a mold suitable to provide a sildenafil citrate rectal suppository, and allowed to cool. The suppository so provided is a unit dosage form suitable for transrectal administration.

EXAMPLE 11

Evaluation of Orally Administered Active Agents in Treating Premature Ejaculation Methods A double-blind randomized crossover study was performed with 31 heterosexual men suffering from primary premature ejaculation, defined for the purpose of the study as an intravaginal ejaculation latency time (IVELT) of less than 2 minutes. Exclusion criteria included the following: (a) history of a psychiatric disorder; (b) current physical illness; (c) previous surgery or drug therapy with an active agent known to affect sexual function; (d) current substance abuse; (e) patients with secondary premature ejaculation combined with erectile dysfunction. All patients were asked not to use condoms or topical penile applications.

Treatment phases comprised five four-week consecutive treatment periods, each separated by a two-week washout period. Each patient was informed that he would be treated with five different modalities of identical action to determine which of the five was most effective. The patients were randomly assigned to receive clomipramine hydrocloride (25 mg), sertraline hydrochloride (50 mg), paroxetine hydrochloride (20 mg), or sildenafil citrate (50 mg), or instructed to use the pause-squeeze technique developed by Masters and Johnson (Masters and Johnson, *Human Sexual Inadequacy,* Little, Brown & Company, Boston, Mass., 1970). The drugs were administered as needed 3 to 5 hours before planned intercourse and not more than twice a week. The pause-squeeze technique was used during intercourse. Each patient was randomly assigned to receive any of the available treatments as the first treatment and a sequence of treatment regimens. The assignment was unknown by the patient. Subjects were asked to complete a questionnaire regarding intravaginal ejaculation latency time of the last two consecutive experiences of intercourse, frequency of intercourse and possible side effects. The first nine items of the sexual satisfaction questionnaire designed by Althof et al. (Althof et al.(1999), "EDITS: Development of Questionnaires for Evaluating Satisfaction with Treatment for Erectile Dysfunction," *Urology* 53:793-399) was used to measure the degree of sexual satisfaction, with higher scores indicating greater satisfaction. All measurements were obtained before treatment, after each treatment and after each washout period. Twenty healthy men who reported a sexual history free of symptoms of premature ejaculation served as a control group.

Statistical analysis: The variables in this study were statistically processed using the SPSS program for MicroSoft Windows®, standard version, release 8.0. The data were subjected to the Kolmogorov-Smirnov one-sample test, to test for normal distribution. This test showed that all the outcome variables were nonparametric. Nonparametric statistical tests were used to assess differences in the measurements. Friedman's two-way analysis of variance was used for comparison between all the treatment periods. Wilcoxon signed rank test was used for evaluation of measures between baseline and after each treatment and also between every two treatment periods. The relationship between parameters was quantified by using the Spearman rank correlation coefficient. Chi-square and Fisher exact tests were used for comparison of the incidence of side effects among different treatments. Student's t-test and Chi-square test were used for comparison between the study group and control group. A two-tailed P-value <0.05 was considered significant.

Results

After four-week treatments with clomipramine, sertraline, paroxetine, sildenafil, and the pause-squeeze technique, the median intravaginal ejaculation latency time was significantly increased from the pretreatment median of 1 minutes to 4 minutes, 3 minutes, 4 minutes, 15 minutes and 3 minutes respectively (Wilcoxon z=−4.54, −4.63, −4.71, −4.63 and −4.55, respectively, all P<0.0001).

According to Friedman's test, treatment with sildenafil caused a significant increase in the median IVELT, median sexual satisfaction score and median IVELT during the washout period (Table 1). The most effective treatment in prolongation of IVELT was sildenafil in 28 patients (90.3%), followed by paroxetine (80.6%), sertraline (71.2%), clomipramine (71%) and the pause-squeeze technique (54.8%). Clomipramine, sertraline and paroxetine were more or less equivalent to each other in terms of ejaculation latency time and sexual satisfaction score (all P>0.05). Paroxetine was found to be superior to the pause-squeeze technique in terms of ejaculatory latency and sexual satisfaction score (Wilcoxon z=−2.05, P=0.04, z=−2.24, P=0.025, respectively).

Sexual satisfaction scores showed statistically significant positive correlation with IVELT during all treatment periods (all P=0.01). There was a significant positive correlation (r=0.666, P=0.01) between anxiety score and IVELT during treatment with the pause-squeeze technique. Moreover, we found significant negative correlation between anxiety score and sexual satisfaction score during treatment with the pause-squeeze technique (r=−0.547, P=0.01), clomipramine (r=−0.381, P<0.05), sildenafil (r=−0.573, P=0.01).

Table 2 displays overall incidence and types of the reported side effects for each treatment. No adverse effects on sexual function were noted, and most of the side effects were mild to moderate in severity.

of IVELT, and the IVELT was increased by a factor of 15, on average. The results demonstrate that a phosphodiesterase inhibitor such as sildenafil is highly effective in the treatment of premature ejaculation.

We claim:

1. A method for treating premature ejaculation, which comprises administering to a male individual in need of such treatment a therapeutically effective amount of an active agent selected from the group consisting of phosphodiesterase inhibitors and pharmaceutically acceptable salts, esters, amides, prodrugs, and active metabolites thereof.

2. The method of claim 1, wherein the active agent is contained within a pharmaceutical formulation.

3. The method of claim 2, wherein the pharmaceutical formulation is a unit dosage form.

4. The method of claim 1, wherein the active agent is administered on an as-needed basis.

TABLE 1

|  | Baseline | Clomipramine | Sertraline | Paroxetine | Sildenafil | Squeeze Technique | Friedman $\chi^2$ | dF | P |
|---|---|---|---|---|---|---|---|---|---|
| Anxiety score |  |  |  |  |  |  |  |  |  |
| Median | 12 | 11 | 11 | 9 | 8 | 12 | 55.15 | 5 | 0.0001 |
| (Range) | (5–25) | (4–22) | (5–22) | (5–23) | (4–15) | (5–21) |  |  |  |
| IVELT (min) |  |  |  |  |  |  |  |  |  |
| Median | 1 | 4 | 3 | 4 | 15 | 3 | 92.53 | 5 | 0.0001 |
| (Range) | (0.5–1.5) | (1–8) | (1–10) | (2–10) | (5–30) | (1–7) |  |  |  |
| Sexual satisfaction score |  |  |  |  |  |  |  |  |  |
| Median |  | 11 | 10 | 12 | 30 | 6 | 57.87 | 4 | 0.0001 |
| (Range) |  | (0–25) | (0–31) | (0–29) | (17–34) | (0–22) |  |  |  |
| IVELT during washout periods (min) |  |  |  |  |  |  |  |  |  |
| Median |  | 1 | 1 | 1 | 1.75 | 1 | 32.52 | 5 | 0.0001 |
| (Range) |  | (0.5–1.5) | (0.5–2) | (0.5–2) | (0.5–8) | (0.5–1.5) |  |  |  |

TABLE 2

|  | SERTRALINE | PAROXETINE | SILDENAFIL | CLOMIPRAMINE |
|---|---|---|---|---|
| No. patients with side effects (%) | 3 (10.3%) | 5 (17.2%) | 5 (17.9%) | 7 (25%) |
| P-value* | 0.27 | 0.69 | 0.75 |  |
| Side effects (no.): |  |  |  |  |
| dry mouth |  |  | 2 | 3 |
| anorexia | 1 |  |  |  |
| nausea | 1 | 1 |  | 1 |
| headache |  |  | 2 |  |
| flushing |  |  | 2 |  |
| drowsiness | 1 |  |  | 1 |
| sleepiness |  |  |  | 2 |
| nasal congestion |  |  |  | 1 |
| yawning |  | 2 |  |  |

*Compared to incidence of side effects with clomipramine

As may be seen, then, treatment with clomipramine, sertraline, paroxetine, sildenafil and the pause-squeeze technique on an "as needed" basis resulted in a statistically significant and clinically relevant delay of intravaginal ejaculation latency time in patients suffering from premature ejaculation. Sildenafil, in particular, was quite effective, insofar as over 90% of patients experienced a prolongation 5. The method of claim 4, wherein the active agent is administered immediately prior to sexual activity.

6. The method of claim 4, wherein the active agent is administered about 0.5 to about 24 hours prior to sexual activity.

7. The method of claim 6, wherein the active agent is administered about 1 to about 12 hours prior to sexual activity.

8. The method of claim 7, wherein the active agent is administered about 1 to about 4 hours prior to sexual activity.

9. The method of any one of claims 5, 6, 7 or 8, wherein the sexual activity is sexual intercourse.

10. The method of claim 2, wherein the formulation is a controlled release dosage form.

11. The method of claim 10, wherein the formulation is a delayed release dosage form.

12. The method of claim 10, wherein the formulation is a sustained release dosage form.

13. The method of claim 11, wherein the formulation is a sustained release dosage form.

14. The method of claim 12, wherein the sustained release dosage form provides drug release over a time period of about 4 to about 48 hours.

15. The method of claim 1, wherein the active agent is administered orally.

16. The method of claim 2, wherein the active agent is administered orally.

17. The method of claim 16, wherein the pharmaceutical formulation is selected from the group consisting of tablets, capsules, caplets, solutions, suspensions syrups granules, beads, powders and pellets.

18. The method of claim 17, wherein the pharmaceutical formulation comprises a tablet.

19. The method of claim 17, wherein the pharmaceutical formulation comprises a capsule.

20. The method of claim 1, wherein the active agent is administered transmucosally.

21. The method of claim 20, wherein the active agent is administered sublingually.

22. The method of claim 20, wherein the active agent is administered buccally.

23. The method of claim 20, wherein the active agent is administered intranasally.

24. The method of claim 20, wherein the active agent is administered transurethrally.

25. The method of claim 20, wherein the active agent is administered rectally.

26. The method of claim 20, wherein the active agent is administered by inhalation.

27. The method of claim 1, wherein the active agent is administered topically.

28. The method of claim 1, wherein the active agent is administered transdermally.

29. The method of claim 1, wherein the active agent is administered parenterally.

30. The method of claim 1, wherein the active agent is selected from the group consisting of Type III phosphodiesterase inhibitors, Type IV phosphodiesterase inhibitors, Type V phosphodiesterase inhibitors, and pharmaceutically acceptable salts, esters, amides, prodrugs, active metabolites, and combinations thereof.

31. The method of claim 30, wherein the active agent is a Type III phosphodiesterase inhibitor.

32. The method of claim 31, wherein the Type III phosphodiesterase inhibitor is selected from the group consisting of bipyridines, imidazolones, imidazolines, dihydropyridazinones, dihydroquinolones, mixed Type III-Type IV inhibitors, anagrelide, bemoradan, ibudilast, isomazole, lixazinone, motapizone, olprinone, phthalazinol, pimobendan, quazinone, siguazodan and trequinsin.

33. The method of claim 32, wherein the Type III phosphodiesterase inhibitor is a bipyridine.

34. The method of claim 33, wherein the bipyridine is selected from the group consisting of amrinone, milrinone and olprinone.

35. The method of claim 30, wherein the active agent is a Type IV phosphodiesterase inhibitor.

36. The method of claim 35, wherein the Type IV phosphodiesterase inhibitor is selected from the group consisting of pyrrolidinones, quinazolinediones, xanthine derivatives, phenyl ethyl pyridines, tetrahydropyrimidones, diazepine derivatives, oxime carbamates, naphthyridinones, benzofurans, naphthalene derivatives, purine derivatives, imidazolidinones, cyclohexane carboxylic acids, benzamides, pyridopyridazinones, benzothiophenes, etazolate, S-(+)-glaucine, substituted phenyl compounds and substituted biphenyl compounds.

37. The method of claim 36, wherein the Type IV phosphodiesterase inhibitor is a pyrrolidinone.

38. The method of claim 37, wherein the pyrrolidinone is rolipram.

39. The method of claim 30, wherein the active agent is a Type V phosphodiesterase inhibitor.

40. The method of claim 39, wherein the Type V phosphodiesterase inhibitor is selected from the group consisting of (S)-2-(2-hydroxymethyl-1-pyrrolidinyl)-4-(3-chloro-4-methoxy-benzylamino)-5-[N-(2-pyrimidinylmethyl) carbamoyl]pyrimidine; 2-(5,6,7,8-tetrahydro-1,7-naphthyridin-7-yl)-4-(3-chloro-4-methoxybenzylamino)-5-[N-(2-morpholinoethyl)carbamoyl]-pyrimidine; (S)-2-(2-hydroxymethyl-1-pyrrolidinyl)-4-(3-chloro-4-methoxybenzylamino)-5-[N-(1,3,5-trimethyl-4-pyrazolyl) carbamoyl]pyrimidine; zaprinast; 1-(3-chloroanilino)-4-phenylphthalazine; dipyridamole; vinpocetine; FR229934; 1-methyl-3-isobutyl-8-methylamino)xanthine; IC-351; methyl 2-(4-aminophenyl)-1,2-dihydro-1-oxo-7-(2-pyridinylmethoxy)-4-(3,4,5-trimethoxyphenyl)-3-isoquinoline carboxylate dihydrochloride; 4-bromo-5-(pyridylmethylamino)-6-[3-(4-chlorophenyl)propoxy]-3 (2H)pyridazinone; 1-[4-[(1,3-benzodioxol-5-ylmethyl) amino]-6-chloro-2-quinazolinyl]-4-piperidine-carboxylic acid; (+)-cis-5,6a,7,9,9,9a-hexahydro-2-[4-(trifluoromethyl)-phenylmethyl-5-methyl-cyclopent-4,5] imidazo[2,1-b]purin-4(3H)one; furazlocillin; cis-2-hexyl-5-methyl-3,4,5,6a,7,8,9,9a-octahydrocyclopent[4,5]imidazo [2,1-b]purin-4-one; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl) amino]-6-chloro-2-quinazolinyl]-4-piperidine carboxylic acid; vardenafil; GF-196960; Sch-51866; sodium 1-[6-chloro-4-(3,4-methylenedioxybenzyl)-aminoquinazolin-2-yl]piperidine-4-carboxylate sesquihydrate; 1,3-dimethyl-6 (2-propoxy-5-methanesulfonamidophenyl)-1,5-dihydropyrazolo[3,4-d]pyrimidin-4-one; and 1-ethyl-3-methyl-6-(2-propoxy-5-(4-methylthiazol-2-yl)phenyl-1,5-dihydropyrazolo[3,4-d]pyrimidin-4-one.

41. The method of claim 39, wherein the Type V phosphodiesterase inhibitor is selected from the group consisting of griseolic acid derivatives, 2-phenylpurinones, phenylpyridones, fused and condensed pyrimidines, pyrimidopyrimidines, purine compounds, quinazoline compounds, phenylpyrimidinones, and imidazoquinoxalinones.

42. The method of claim 39, wherein the Type V phosphodiesterase inhibitor is selected from the group consisting of sildenafil, zaprinast, dipyridamole, (S)-2-(2-hydroxymethyl-1-pyrrolidinyl)-4-(3-chloro-4-methoxybenzylamino)-5-[N-(2-pyrimidinylmethyl)carbamoyl] pyrimidine, 2-(5,6,7,8-tetrahydro-1,7-naphthyridin-7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxybenzylamino)-5-[N-(1,3,5-trimethyl-4-pyrazolyl) carbamoyl]pyrimidine, and pharmaceutically acceptable salts thereof.

43. The method of claim 42, wherein the Type V phosphodiesterase inhibitor is sildenafil or a pharmaceutically acceptable salt thereof.

44. The method of claim 43, wherein the Type V phosphodiesterase inhibitor is sildenafil citrate.

45. The method of claim 1, wherein the active agent is a nonspecific phosphodiesterase inhibitor selected from the group consisting of theophylline, theobromine, IBMX, pentoxifylline and papaverine.

46. The method of claim 2, wherein the pharmaceutical formulation further comprises an additional active agent.

47. The method of claim 46, wherein the additional active agent is selected from of antidepressant drugs, serotonin agonists, serotonin antagonists, adrenergic agonists, adrenergic antagonists, adrenergic neurone blockers, and derivatives and analogs thereof.

48. The method of claim 47, wherein the agent is an antidepressant drug.

49. The method of claim 48, wherein the antidepressant drug is selected from the group consisting of amesergide, amineptine, amitriptyline, amoxapine, benactyzine, brofaromine, bupropion, butriptyline, cianopramine, citalopram, clomipramine, clorgyline, clovoxamine, dapoxetine, demexiptiline, desipramine, dibenzepin, dimetacrine, dothiepin, doxepin, duloxetine, etoperidone, femoxetine, fezolamine, fluoxetine, fluvoxamine, ifoxetine, imipramine, iprindole, isocarboxazid, levoprotiline, lofepramine, maprotiline, medifoxamine, melitracen, metapramine, methylphenidate, mianserin, milnacipran, minaprine, mirtazapine, moclobemide, nefazodone, nialamide, nomifensine, nortriptyline, opipramol, oxaflozane, oxaprotiline, oxitriptan, paroxetine, phenelzine, pirlindole, propizepine, protriptyline, quinupramine, rolipram, selegiline, sertraline, setiptiline, sibutramine, teniloxazine, tianeptine, tofenacin, toloxatone, tranylcypromine, trazodone, trimipramine, tryptophan, venlafaxine, viloxazine, viqualine, zimeldine, and combinations thereof.

50. The method of claim 47, wherein the agent is a serotonin agonist.

51. The method of claim 50, wherein the serotonin agonist is a 5-HT$_4$ agonist.

52. The method of claim 51, wherein the 5-HT$_4$ agonist is selected from the group consisting of cisapride and nor-cisapride.

53. The method of claim 47, wherein the agent is a serotonin antagonist.

54. The method of claim 53, wherein the serotonin agonist is a 5-HT$_3$ antagonist.

55. The method of claim 54, wherein the 5-HT$_3$ antagonist is selected from the group consisting of ondansetron, ergot alkaloids, granisetron, trimethobenzamide, tropisetron, dolasetron, batanopride and zacopride.

56. A pharmaceutical formulation for treating premature ejaculation and adapted for transmucosal drug administration, comprising a therapeutically effective amount of a phosphodiesterase inhibitor and a carrier suitable for transmucosal drug delivery buccally, sublingually, intranasally, rectally, or by inhalation.

57. The formulation of claim 56, comprising a solid dosage form for application to the buccal mucosa, and wherein the carrier is suitable for buccal drug delivery.

58. The formulation of claim 57, wherein the carrier is a hydrolyzable polymer.

59. The formulation of claim 57, wherein the dosage form further comprises an adhesive suitable for affixing the dosage form to the buccal mucosa.

60. The formulation of claim 56, comprising a dosage form for application to the sublingual mucosa, and wherein the carrier is suitable for sublingual drug delivery.

61. The formulation of claim 56, comprising a dosage form for application to the rectal mucosa, and the carrier is suitable for rectal drug delivery.

62. The formulation of claim 61, comprising a rectal suppository.

63. The formulation of claim 56, comprising a dosage form suitable for inhalation.

64. The formulation of claim 63, comprising a liquid.

65. The formulation of claim 63, comprising a dry powder.

66. The formulation of claim 63, comprising an aerosol composition.

67. The formulation of claim 1, wherein the active agent is selected from the group consisting of Type III phosphodiesterase inhibitors, Type IV phosphodiesterase inhibitors, Type V phosphodiesterase inhibitors, and pharmaceutically acceptable salts, esters, amides, prodrugs, active metabolites, and combinations thereof.

68. The formulation of claim 67, wherein the active agent is a Type III phosphodiesterase inhibitor.

69. The formulation of claim 68, wherein the Type III phosphodiesterase inhibitor is selected from the group consisting of bipyridines, imidazolones, imidazolines, dihydropyridazinones, dihydroquinolones, mixed Type III-Type IV inhibitors, anagrelide, bemoradan, ibudilast, isomazole, lixazinone, motapizone, olprinone, phthalazinol, pimobendan, quazinone, siguazodan and trequinsin.

70. The formulation of claim 69, wherein the Type III phosphodiesterase inhibitor is a bipyridine.

71. The formulation of claim 70, wherein the bipyridine is selected from the group consisting of amrinone, milrinone and olprinone.

72. The formulation of claim 67, wherein the active agent is a Type IV phosphodiesterase inhibitor.

73. The formulation of claim 72, wherein the Type IV phosphodiesterase inhibitor is selected from the group consisting of pyrrolidinones, quinazolinediones, xanthine derivatives, phenyl ethyl pyridines, tetrahydropyrimidones, diazepine derivatives, oxime carbamates, naphthyridinones, benzofurans, naphthalene derivatives, purine derivatives, imidazolidinones, cyclohexane carboxylic acids, benzamides, pyridopyridazinones, benzothiophenes, etazolate, S-(+)-glaucine, substituted phenyl compounds and substituted biphenyl compounds.

74. The formulation of claim 73, wherein the Type IV phosphodiesterase inhibitor is a pyrrolidinone.

75. The formulation of claim 74, wherein the pyrrolidinone is rolipram.

76. The formulation of claim 67, wherein the active agent is a Type V phosphodiesterase inhibitor.

77. The formulation of claim 76, wherein the Type V phosphodiesterase inhibitor is selected from the group consisting of: (S)-2-(2-hydroxymethyl-1-pyrrolidinyl)-4-(3-chloro-4-methoxy-benzylamino)-5-[N-(2-pyrimidinylmethyl)-carbamoyl]pyrimidine; 2-(5,6,7,8-tetrahydro-1,7-naphthyridin-7-yl)-4-(3-chloro-4-methoxybenzylamino)-5-[N-(2-morpholinoethyl)carbamoyl]-pyrimidine; (S)-2-(2-hydroxymethyl-1-pyrrolidinyl)-4-(3-chloro-4-methoxy-benzylamino)-5-[N-(1,3,5-trimethyl-4-pyrazolyl)carbamoyl]pyrimidine; zaprinast; 1-(3-chloroanilino)-4-phenylphthalazine; dipyridamole; vinpocetine; FR229934; 1-methyl-3-isobutyl-8-(methylamino)xanthine; IC-351; methyl 2-(4-aminophenyl)-1,2-dihydro-1-oxo-7-(2-pyrdinylmethoxy)-4-(3,4,5-trimethoxyphenyl)-3-isoquinoline carboxylate dihydrochloride; 4-bromo-5-(pyridylmethylamino)-6-[3-(4-chlorophenyl)propoxy]-3(2H)pyridazinone; 1-[4-[(1,3-benzodioxol-5-ylmethyl)amino]-6-chloro-2-quinazolinyl]-4-piperidine-carboxylic acid; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]imidazo[2,1-b]purin-4-one; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5-(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidine carboxylic acid; vardenafil; GF-196960; Sch-51866; sodium 1-[6-chloro-4-(3,4-methylenedioxybenzyl)-aminoquinazolin-2-yl]piperidine4-carboxylate sesquihydrate; 1,3-dimethyl-6(2-propoxy-5-methanesulfonamidophenyl)-1,5-dihydropyrazolo[3,4-d]pyrimidin-4-one; and 1-ethyl-3-methyl-6-(2-propoxy-5-(4-methylthiazol-2-yl)phenyl-1,5-dihydropyrazolo[3,4-d]pyrimidin-4-one.

78. The formulation of claim 76, wherein the Type V phosphodiesterase inhibitor is selected from the group consisting of griseolic acid derivatives, 2-phenylpurinones, phenylpyridones, fused and condensed pyrimidines, pyrimidopyrimidines, purine compounds, quinazoline compounds, phenylpyrimidinones, and imidazoquinoxalinones.

79. The formulation of claim 76, wherein the Type V phosphodiesterase inhibitor is selected from the group consisting of sildenafil, zaprinast, dipyridamole, (S)-2-(2-hydroxymethyl-1-pyrrolidinyl)-4-(3-chloro4-methoxybenzylamino)-5-[N-(2-pyrimidinylmethyl)carbamoyl]pyrimidine, 2-(5,6,7,8-tetrahydro-1,7-naphthyridin-7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxybenzylamino)-5-[N-(1,'3,5-trimethyl-4-pyrazolyl)carbamoyl]pyrimidine, and pharmaceutically acceptable salts thereof.

80. The formulation of claim 79, wherein the Type V phosphodiesterase inhibitor is sildenafil or a pharmaceutically acceptable salt thereof.

81. The formulation of claim 80, wherein the Type V phosphodiesterase inhibitor is sildenafil citrate.

82. The formulation of claim 67, wherein the active agent is a nonspecific phosphodiesterase inhibitor selected from the group consisting of theophylline, theobromine, IBMX, pentoxifylline and papaverine.

83. The formulation of claim 67, wherein the pharmaceutical formulation further comprises an additional active agent.

84. The formulation of claim 83, wherein the additional active agent is selected from of antidepressant drugs, serotonin agonists, serotonin antagonists, adrenergic agonists, adrenergic antagonists, adrenergic neurone blockers, and derivatives and analogs thereof.

85. The formulation of claim 84, wherein the agent is an antidepressant drug.

86. The formulation of claim 85, wherein the antidepressant drug is selected from the group consisting of amesergide, amineptine, amitriptyline, amoxapine, benactyzine, brofaromine, bupropion, butriptyline, cianopramine, citalopram, clomipramine, clorgyline, clovoxamine, dapoxetine, demexiptiline, desipramine, dibenzepin, dimetacrine, dothiepin, doxepin, duloxetine, etoperidone, femoxetine, fezolamine, fluoxetine, fluvoxamine, ifoxetine, imipramine, iprindole, isocarboxazid, levoprotiline, lofepramine, maprotiline, medifoxamine, melitracen, metapramine, methylphenidate, mianserin, milnacipran, minaprine, mirtazapine, moclobemide, nefazodone, nialamide, nomifensine, nortriptyline, opipramol, oxaflozane, oxaprotiline, oxitriptan, paroxetine, phenelzine, pirlindole, propizepine, protriptyline, quinupramine, rolipram, selegiline, sertraline, setiptiline, sibutramine, teniloxazine, tianeptine, tofenacin, toloxatone, tranylcypromine, trazodone, trimipramine, tryptophan, venlafaxine, viloxazine, viqualine, zimeldine, and combinations thereof.

87. The formulation of claim 84, wherein the agent is a serotonin agonist.

88. The formulation of claim 87, wherein the serotonin agonist is a 5-$HT_4$ agonist.

89. the formulation of claim 88, wherein the 5-$HT_4$ agonist is selected from the group consisting of cisapride and norcisapride.

90. The formulation of claim 84, wherein the agent is a serotonin antagonist.

91. The formulation of claim 90, wherein the serotonin agonist is a 5-$HT_3$ antagonist.

92. The formulation of claim 91, wherein the 5-$HT_3$ antagonist is selected from the group consisting of ondansetron, ergot alkaloids, granisetron, trimethobenzamide, tropisetron, dolasetron, batanopride and zacopride.

93. A packaged kit for a patient to use in the treatment of premature ejaculation, comprising: a pharmaceutical formulation of a phosphodiesterase inhibitor; a container housing the pharmaceutical formulation during storage and prior to administration; and instructions for carrying out drug administration in a manner effective to treat premature ejaculation.

94. The packaged kit of claim 93, wherein the pharmaceutical formulation is an oral dosage form containing a unit dosage of the phosphodiesterase inhibitor, the unit dosage being a therapeutically effective dosage for treatment of premature ejaculation.

* * * * *